United States Patent [19]

Lehr et al.

[11] 4,011,875

[45] Mar. 15, 1977

[54] MEDICAL ELECTRODES

[76] Inventors: Siegfried R. Lehr, Mottlst. 17, D8 Munich 40; Alfred Schaudig, Athosstr. 9a, 8 Munich, both of Germany

[22] Filed: Feb. 25, 1974

[21] Appl. No.: 447,241

[30] Foreign Application Priority Data

Feb. 27, 1973 Germany .......................... 2309749

[52] U.S. Cl. .............................. 128/418; 128/419 P
[51] Int. Cl.² ............................................. A61N 1/04
[58] Field of Search ............... 128/404, 418, 419 P, 128/DIG. 4, 2.06 E, 2.1, 214.4

[56] References Cited

UNITED STATES PATENTS

| 2,831,174 | 4/1958 | Hilmo ............................... 128/2.1 E |
| 3,120,227 | 2/1964 | Hunter, Jr. et al. ................ 128/418 |
| 3,786,810 | 1/1974 | Pannier, Jr. et al. ............ 128/214.4 |
| 3,800,784 | 4/1974 | Kiszel et al. ........................ 128/418 |

*Primary Examiner*—William E. Kamm

[57] ABSTRACT

An attachable and detachable medical electrode, e.g. for pacemakers with hooks, remotely actuable from the end of the electrode by a guide stylet or a guide catheter, closing by resilient means, opening either by resilience or by spreading means.

3 Claims, 5 Drawing Figures

MEDICAL ELECTRODES

THE INVENTION

The invention relates to medical electrodes, in particular to pacemaker electrodes, supplied with a fixation mechanism, which, when actuated, attaches or detaches the electrode. Such electrodes are used, e.g., in the therapy of many disorders of the electrical activity of the heart. One known electrode uses diverging resilient wire tips, supposed to penetrate the heart muscle as barbs; another one uses synthetic brushes, pushed out and pulled in through oblique channels in the electrode tip, for fixation. The inherent disadvantage of such fixations is that the relatively long, spreaded wire tips or brushes may cause bleeding of the heart muscle by traumatization and may even lead to perforation. Furthermore the fixation is not sufficiently secure against strong abrupt movements.

The invention provides a secure fixation of electrodes, using only a small depth of the muscle in comprising fixation means formed by two hooks, closeable like jaws; the tips of the hooks are tapered such as to complete themselves to a full cross sectional area like the round parts of the hooks. The clawlike closing of the two hooks may be done by their own resilience, respectively the resilience of their legs and the opening by moving a spreading means, actuating said legs, while the closing force of the hooks may be assisted by a coil spring surrounding the legs of the hooks; or the hooks may open by their own resilience and are closed in pulling their legs in a preferably cylindrical enclosure which may be a compression coil spring, pulling the hooks in closing position and securing them there.

The legs opposite to the hooks are preferably joined together or made in one part. For raising the resilience, the legs opposite to the hooks, including their joining, are weakened, e.g. by grinding, as legs and hooks are made of spring steel.

Actuating means for opening and closing of the hooks may be a guide stylet or a guide catheter.

THE DRAWING

DESCRIPTION

Figure 1:
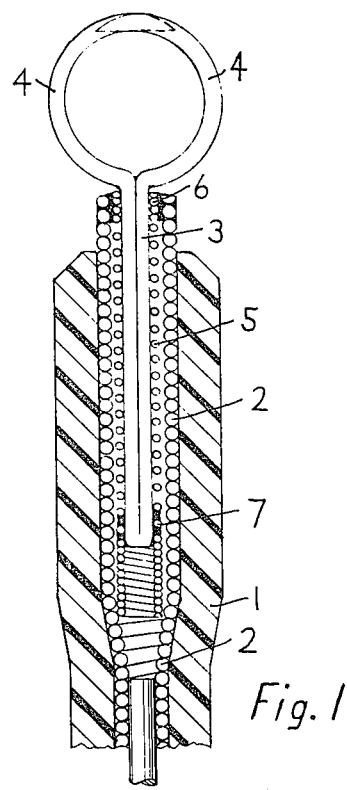
FIG. 1 is a longitudinal section of an electrode with hooks opening by resilience, actuated by stylet.

In the electrode of FIG. 1 the two joined legs 3 of the half-circle shaped hooks 4 inclusive the surrounding coil spring 5 are inserted in the coiled cable 2, insulated with the hose 1. The winding sense of the coil spring 5 is opposite to the winding sense of the coiled cable; the stop wound rear of the coil spring 5 serves as stylet funnel. Stop wound means wound so that the windings touch each other. Stop wound is used e.g. in Rocky Mountains dental catalog. As the front end 6 is fastened, e.g. by tucking in of the first winding of the coiled cable 2 and the rear end of the legs 7 fastened preferably by adhesive to the coil spring 5, the latter tends to pull the legs 3 of the hooks 4 into the tip of the electrode, thus closing the hooks 4 clawlike.

In this position the electrode is implanted transvenously in a chamber of the heart until the tip, with the hooks being the stimulating surface, touches the muscle. When a satisfactory threshold is measured, a stylet, is pushed forward, holding the cable 2 fixed; the legs 3 move forward until the coil spring 5 is compressed completely, opening the hooks 4; when the stylet is released the hooks close clawlike, their tips piercing the muscle tissue.

Figure 2:
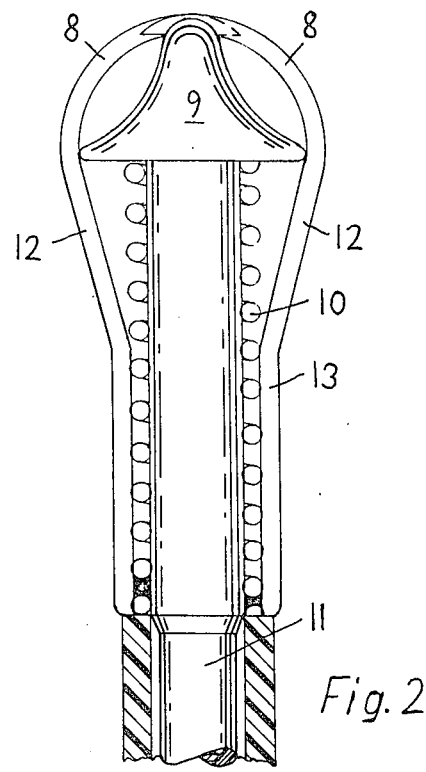
FIG. 2 shows a longitudinal section of an electrode with hooks closing by resilience, actuated by guide catheter.
Figure 3:
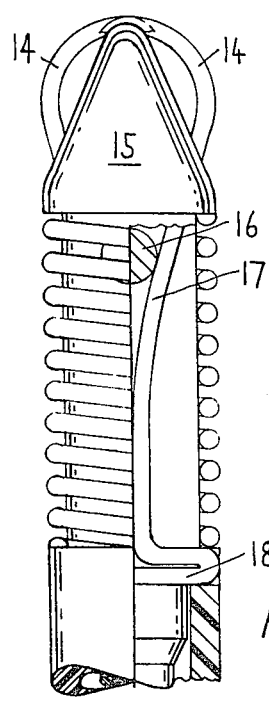
FIG. 3 is a half longitudinal section of an electrode with hooks closing by resilience.

The embodiment of FIG. 2 shows both hooks 8 closed in general by resilience. To open the hooks, the spreading means 9 is retracted through the cable 11 against the pressure of the spring 10, keeping the guide catheter fixed; thereby the rim of the spreading means 9 forces the oblique legs 12 and legs 13 outward. When released, the hooks close. The embodiment of FIG. 3 shows hooks, also closing by resilience; the opening of the hooks is done by relative movement of the tip 15 to the hooks 14, the bolt 16 in the tip 15 spreading the oblique legs 17, being connected integral at 18.

Figure 4:
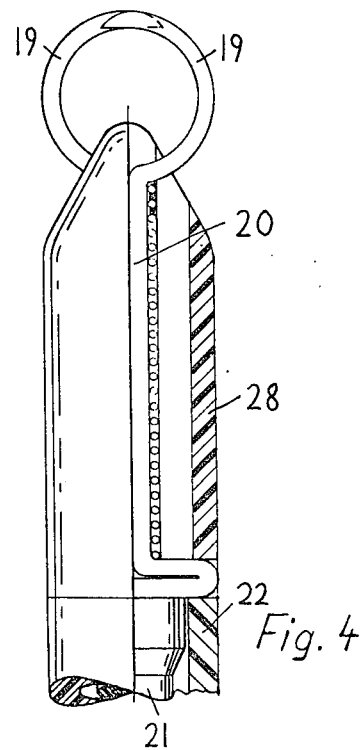
FIG. 4 is also an electrode but with hooks opening by resilience.

FIG. 4 is an electrode with hooks 19, opening by resilience of their legs 20 when said legs are pushed out of the tip through pulling on the cable 21, while the guide catheter 22 is held fast.

Figure 5:
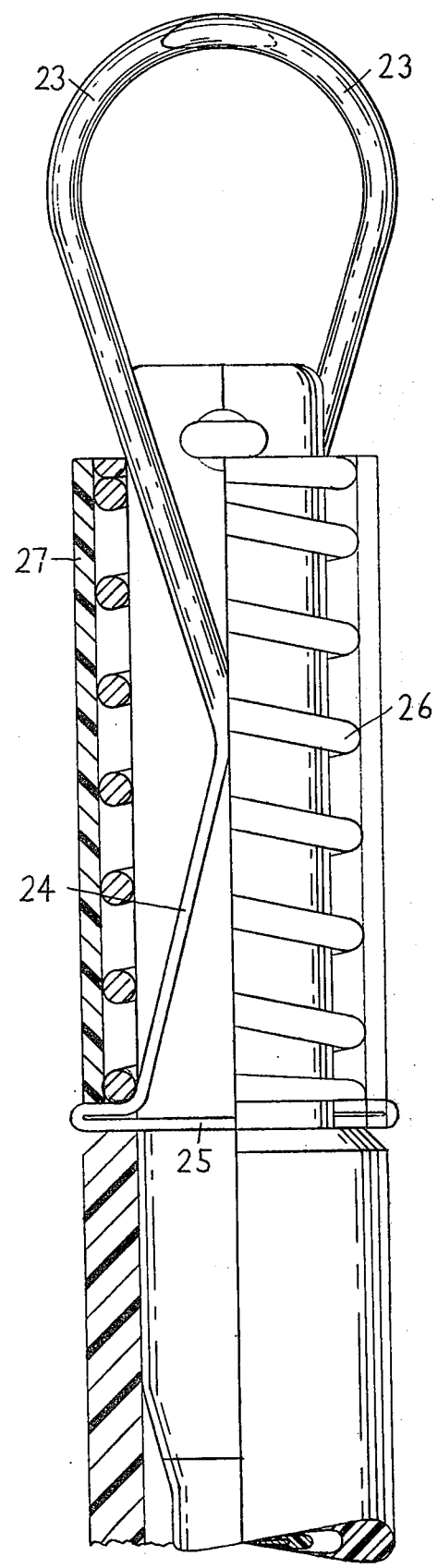
FIG. 5 shows another embodiment with hooks opening by resilience.

FIG. 5 shows the ends 24 opposite to the hooks 23 and their connection 25 weakened by grinding to increase the opening of the hooks by greater resilience. The coil spring 26 is insulated by a hose 27 analogous to the hose 28 in FIG. 4. Insulation may also be done by oxidation of metal parts.

I claim:

1. A medical electrode for implantation in a body, comprising a hollow conductor, 2 forcep-like hooks at the tip of the electrode, having legs connected together, said hooks opening by resilience of said legs, a compression coil spring around said legs, forcing said legs into itself, thus closing said hooks and a guide stylet for remotely opening said hooks.

2. The invention as defined in claim 1, said guide stylet being centered by the end of said compression coil spring, said end being stop wound.

3. A medical electrode for implantation in a body, comprising a non-hollow conductor, 2 forcep-like hooks having legs connected together, said hooks opening by resilience of said legs, a compression coil spring closing said hooks and a guide catheter for remotely opening said hooks.

* * * * *